United States Patent
Gotou et al.

(10) Patent No.: US 9,732,027 B2
(45) Date of Patent: Aug. 15, 2017

(54) PRODUCTION METHOD FOR ALPHA-FLUORO ACRYLIC ACID ESTERS

(71) Applicant: DAIKIN INDUSTRIES, LTD., Osaka (JP)

(72) Inventors: Akihiro Gotou, Osaka (JP); Manaho Miyazaki, Osaka (JP); Sumi Ishihara, Osaka (JP); Takashi Namikawa, Osaka (JP); Tatsuya Ohtsuka, Osaka (JP); Yosuke Kishikawa, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 15/107,204

(22) PCT Filed: Dec. 26, 2014

(86) PCT No.: PCT/JP2014/084633
§ 371 (c)(1),
(2) Date: Jun. 22, 2016

(87) PCT Pub. No.: WO2015/099154
PCT Pub. Date: Jul. 2, 2015

(65) Prior Publication Data
US 2016/0318842 A1    Nov. 3, 2016

(30) Foreign Application Priority Data

Dec. 27, 2013  (JP) .................................. 2013-272016
Feb. 28, 2014  (JP) .................................. 2014-038757

(51) Int. Cl.
*C07C 67/36* (2006.01)
(52) U.S. Cl.
CPC ..................................... *C07C 67/36* (2013.01)
(58) Field of Classification Search
CPC ................................ C07C 51/14; C07C 67/36
See application file for complete search history.

(56) References Cited

U.S. PATENT DOCUMENTS

| 4,792,620 | A | * | 12/1988 | Paulik | .................. | B01J 31/0231 |
| | | | | | | 560/232 |
| 5,231,219 | A | | 7/1993 | Grison et al. | | |
| 5,972,839 | A | | 10/1999 | Ziemer et al. | | |
| 2015/0191413 | A1 | | 7/2015 | Ohtsuka et al. | | |

FOREIGN PATENT DOCUMENTS

| DE | 101 51 492 | 5/2002 |
| JP | 60-158136 | 8/1985 |
| JP | 5-201921 | 8/1993 |
| JP | 2001-506643 | 5/2001 |
| JP | 2005-325042 | 11/2005 |
| WO | 2014/034906 | 3/2014 |

OTHER PUBLICATIONS

Xu et al, Journal of Organic Chemistry, Highly Stereoselective Synthesis of (E) and (Z)-alpha-Fluoro-alpha, beta-.Unsaturated Esters and (E) and (Z)-alpha-Fluoro-alpha, beta-.Unsaturated Amides from 1-Bromo-1-fluoroalkenes via Palladium-Catalyzed Carbonylation Reactions, 2005, 70 pp. 4346-4353.*
International Search Report issued Mar. 17, 2015 in corresponding (PCT) Application No. PCT/JP2014/084633.
Extended European Search Report dated Apr. 28, 2017 in corresponding European Application No. 14875459.1.
Xu et al., "Kinetic Separation Methodology for the Stereoselective Synthesis of (E)- and (Z)-α-Fluoro-α,β-unsaturated Esters via the Palladium-Catalyzed Carboalkoxylation of 1-Bromo-1-fluoroalkenes", Organic Letters, 4(5):831-833 (2002).
Wesolowski et al., "Palladium-Catalyzed Stereospecific Carboalkoxylation of 1,2-Difluoro-1-iodoalkenes and α,β-Difluoro-β-iodostyrenes", Tetrahedron Letters, 40(12):2243-2246 (1999).

(Continued)

*Primary Examiner* — Paul A Zucker
(74) *Attorney, Agent, or Firm* — Wenderoth, Lind & Ponack, L.L.P.

(57) ABSTRACT

An object of the present invention is to provide a process for producing α-fluoroacrylic acid esters at a high starting material conversion and a high yield. The present invention provides, as a means to achieve the object, a process for producing a compound represented by formula (1):

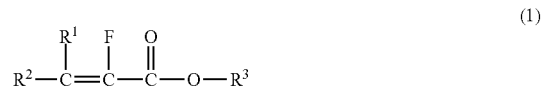

wherein $R^1$ and $R^2$ are the same or different and each represent alkyl, fluoroalkyl, aryl optionally substituted with at least one substituent, halogen, or hydrogen; and $R^3$ represents alkyl, fluoroalkyl, or aryl optionally substituted with at least one substituent, the process comprising step A of reacting a compound represented by formula (2):

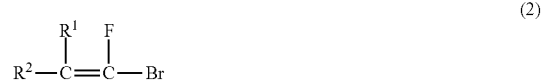

wherein the symbols are as defined above, with carbon monoxide and an alcohol represented by formula (3):

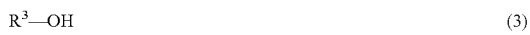

wherein the symbol is as defined above, in the presence of a transition metal complex catalyst containing at least one bidentate phosphine ligand and a base to thereby obtain the compound represented by formula (1).

6 Claims, No Drawings

(56) References Cited

OTHER PUBLICATIONS

Schoenberg et al., "Palladium-Catalyzed Carboalkoxylation of Aryl, Benzyl, and Vinylic Halides", Journal of Organic Chemistry, 39(23):3318-3326 (1974).
Doherty et al., "Selectivity for the methoxycarbonylation of ethylene versus CO-ethylene copolymerization with catalysts based on $C_4$-bridged bidentate phosphines and phospholes", Journal of Organometallic Chemistry, vol. 640, 2001, pp. 182-196.

* cited by examiner

PRODUCTION METHOD FOR ALPHA-FLUORO ACRYLIC ACID ESTERS

TECHNICAL FIELD

The present invention relates to a process for producing α-fluoroacrylic acid esters.

BACKGROUND ART

α-Fluoroacrylic acid esters are useful, for example, as a synthetic intermediate for medical drugs (e.g., antibiotic drugs), a synthetic intermediate for cladding materials of optical fibers, a synthetic intermediate for painting materials, a synthetic intermediate for semiconductor resist materials, and a monomer for functional polymers.

Examples of conventional processes for producing an α-fluoroacrylic acid ester in an excellent yield include the process proposed in Patent Document 1 for producing an α-fluoroacrylic acid ester by subjecting an α-fluorophosphono acetate and paraformaldehyde to a condensation reaction, the process being characterized in that the condensation reaction is carried out in an aqueous medium in the presence of a weak inorganic base (Patent Literature 1).

CITATION LIST

Patent Literature

Patent Literature 1: JPH05-201921A

SUMMARY OF INVENTION

Technical Problem

The yield of α-fluoroacrylic acid ester according to the process disclosed in Patent Document 1, however, is 82% at most, and a process for achieving a higher yield is desired.

In particular, it is desirable that synthetic intermediates, for example, for producing medical drugs, contain by-products in an extremely low amount from the standpoint of medical drug safety; thus, a high selectivity of α-fluoroacrylic acid ester is required. Nonetheless, in the conventional processes for producing a 2-fluoroacrylic acid compound, the reaction is typically complicated because of the generation of derivatives or so on; the yield of the 2-fluoroacrylic acid compound is low; and the separation of the 2-fluoroacrylic acid compound is difficult. Therefore, conventional processes have a disadvantage in industrial application in that by-products must be removed to increase the purity of the 2-fluoroacrylic acid compound, whereby large amounts of waste fluids and waste materials are produced.

The present inventors thus developed the following process for producing α-fluoroacrylic acid esters at a high starting material conversion, a high selectivity, and a high yield, and filed a patent application (PCT/JP2013/073446, unpublished) for the process for producing a compound represented by formula (1'):

(1')

wherein R represents alkyl optionally substituted with at least one fluorine atom, the process comprising step A of
reacting a compound represented by formula (2'):

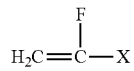
(2')

wherein X represents a bromine atom or a chlorine atom, with carbon monoxide and an alcohol represented by formula (3'):

R—OH (3')

wherein the symbol is as defined above, in the presence of a transition metal catalyst and a base to thereby obtain the compound represented by formula (1').

However, the inventors further aimed to provide a process for producing α-fluoroacrylic acid esters at a high starting material conversion and a high yield using a small amount of a catalyst.

Solution to Problem

The present inventors found that a compound represented by formula (1), which is an α-fluoroacrylic acid ester, is produced by the following process at a high starting material conversion and a high yield, and completed the present invention.

A process for producing a compound represented by formula (1)

(1)

wherein $R^1$ and $R^2$ are the same or different and each represent alkyl, fluoroalkyl, aryl optionally substituted with at least one substituent, halogen, or hydrogen; and
$R^3$ represents alkyl, fluoroalkyl, or aryl optionally substituted with at least one substituent,
the process comprising step A of
reacting a compound represented by formula (2):

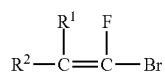
(2)

wherein the symbols are as defined above, with carbon monoxide and an alcohol represented by formula (3):

$R^3$—OH (3)

wherein the symbol is as defined above, in the presence of a transition metal complex catalyst containing at least one bidentate phosphine ligand and a base.

Specifically, the present invention encompasses the following subject matter.

Item 1.

A process for producing a compound represented by formula (1):

$$R^2-\underset{\underset{R^1}{|}}{C}=\underset{\underset{F}{|}}{C}-\underset{}{\overset{O}{\overset{\|}{C}}}-O-R^3 \quad (1)$$

wherein $R^1$ and $R^2$ are the same or different and each represent alkyl, fluoroalkyl, aryl optionally substituted with at least one substituent, halogen, or hydrogen; and $R^3$ represents alkyl, fluoroalkyl, or aryl optionally substituted with at least one substituent, the process comprising step A of reacting a compound represented by formula (2):

$$R^2-\underset{\underset{R^1}{|}}{C}=\underset{\underset{F}{|}}{C}-Br \quad (2)$$

wherein the symbols are as defined above, with carbon monoxide and an alcohol represented by formula (3):

$$R^3-OH \quad (3)$$

wherein the symbol is as defined above, in the presence of a transition metal complex catalyst containing at least one bidentate phosphine ligand and a base to thereby obtain the compound represented by formula (1).

Item 2.

The process according to Item 1, wherein $R^1$ represents hydrogen or aryl, and $R^2$ represents hydrogen or aryl.

Item 3.

The process according to Item 1 or 2, wherein the transition metal is palladium.

Item 4.

The process according to any one of Items 1 to 3, wherein the at least one bidentate phosphine ligand contains two aromatic rings that are linked through an oxygen-containing linking group.

Item 5.

The process according to any one of Items 1 to 4, wherein the transition metal complex catalyst is used in an amount of 0.001 moles or less per mole of the compound represented by formula (2).

Item 6.

The process according to any one of Items 1 to 5, wherein the base is an amine.

Item 7.

The process according to any one of Items 1 to 6, wherein step A is performed at a temperature within the range of 60 to 120° C.

Advantageous Effects of Invention

The process according to the present invention enables the production of α-fluoroacrylic acid esters at a high starting material conversion and a high yield.

DESCRIPTION OF EMBODIMENTS

As used herein, examples of "alkyl" include $C_{1-6}$ alkyl, such as methyl, ethyl, propyl, isopropyl, butyl, isobutyl, sec-butyl, tert-butyl, pentyl, neopentyl, and hexyl.

As used herein, "fluoroalkyl" refers to alkyl having at least one hydrogen atom replaced with a fluorine atom. "Fluoroalkyl" encompasses perfluoroalkyl. "Perfluoroalkyl" refers to alkyl having all hydrogen atoms replaced with fluorine atoms.

As used herein, "alkoxy" refers to alkyl-O— group.

As used herein, examples of "acyl" include alkanoyl (i.e., alkyl-CO— group).

As used herein, examples of "ester group" include alkyl carbonyl oxy (i.e., alkyl-CO—O— group), and alkoxy carbonyl (i.e., alkyl-O—CO— group).

As used herein, examples of "cycloalkyl" include $C_{3-8}$ cycloalkyl, such as cyclopentyl, cyclohexyl, and cycloheptyl.

As used herein, examples of "aryl" include $C_{6-10}$ aryl, such as phenyl and naphthyl.

The process of the present invention for producing a compound represented by formula (1):

$$R^2-\underset{\underset{R^1}{|}}{C}=\underset{\underset{F}{|}}{C}-\underset{}{\overset{O}{\overset{\|}{C}}}-O-R^3 \quad (1)$$

wherein $R^1$ and $R^2$ are the same or different and each represent alkyl optionally substituted with at least one substituent, aryl optionally substituted with at least one substituent, halogen, or hydrogen; and $R^3$ represents alkyl, fluoroalkyl, or aryl optionally substituted with at least one substituent comprises:

step A of reacting a compound represented by formula (2):

$$R^2-\underset{\underset{R^1}{|}}{C}=\underset{\underset{F}{|}}{C}-Br \quad (2)$$

wherein the symbols are as defined above, with carbon monoxide and an alcohol represented by formula (3):

$$R^3-OH \quad (3)$$

wherein the symbol is as defined above, in the presence of a transition metal complex catalyst containing at least one bidentate phosphine ligand and a base to thereby obtain the compound represented by formula (1).

Preferable examples of the substituent in "aryl optionally substituted with at least one substituent" represented by $R^1$ include fluorine, alkoxy, acyl, ester group, cyano, nitro, alkyl, and fluoroalkyl, and more preferable examples include fluorine.

$R^1$ is preferably hydrogen or aryl, and is particularly preferably hydrogen.

Preferable examples of the substituent in "aryl optionally substituted with at least one substituent" represented by $R^2$ include fluorine, alkoxy, acyl, ester group, cyano, nitro, alkyl, and fluoroalkyl, and more preferable examples include fluorine.

$R^2$ is preferably hydrogen or aryl, and is particularly preferably hydrogen.

$R^3$ is preferably methyl, ethyl, or fluoroalkyl, and is particularly preferably methyl.

In a preferable embodiment of the present invention, $R^1$ is hydrogen or aryl, and $R^2$ is hydrogen or aryl.

The compound represented by formula (1) is preferably 2-fluoroacrylic acid methyl ester or 2-fluoroacrylic acid ethyl ester, and is particularly preferably 2-fluoroacrylic acid methyl ester.

The compound represented by formula (2) is a known compound that can be produced by a known process, or is commercially available.

The alcohol represented by formula (3) is preferably methanol, ethanol, trifluoroethanol, pentafluoropropanol, or hexafluoroisopropanol, and is particularly preferably methanol.

The alcohol represented by formula (3) can also serve as a solvent for the reaction in step A.

The alcohol represented by formula (3) used as a reaction starting material for step A is used in an amount of typically 1 to 500 moles, and preferably about 1.1 to 50 moles per mole of the compound represented by formula (2).

When the alcohol represented by formula (3) is also used as a solvent for the reaction in step A, the alcohol is used in large excess relative to the amount of the compound represented by formula (2). Specifically, when a solvent other than the alcohol is not used, the alcohol may be used in an amount of typically 0.1 to 20 L, preferably about 0.2 to 5 L, or 0.5 to 10 L, or about 1 to 5 L per mole of the compound represented by formula (2).

The reaction pressure in step A is not particularly limited, and may be, for example, atmospheric pressure, or a pressure higher than atmospheric pressure. Step A is preferably carried out in a container such as an autoclave, and the carbon monoxide used as a reactant of step A can be introduced into the container by using a carbon monoxide-containing gas, such as purified carbon monoxide gas. The pressure of carbon monoxide is typically 0 to 10 MPaG, and preferably 0.25 to 4 MPaG.

The "transition metal complex catalyst containing at least one bidentate phosphine ligand" used in step A contains, for example, at least one transition metal selected from the group consisting of nickel, palladium, platinum, rhodium, ruthenium, iridium, and cobalt.

Specifically, examples of transition metal complex catalysts usable in step A include nickel complex catalysts, palladium complex catalysts, platinum complex catalysts, rhodium complex catalysts, ruthenium complex catalysts, iridium complex catalysts, and cobalt complex catalysts. The palladium complex catalysts are preferably zero-valent palladium complex catalysts, or divalent palladium complex catalysts.

The transition metal is preferably selected from the group consisting of nickel, cobalt, and palladium, and is particularly preferably palladium.

The "bidentate phosphine ligand" in the "transition metal complex catalyst containing at least one bidentate phosphine ligand" used in step A can be, for example, a bidentate phosphine ligand in which at least one substituent selected from the group consisting of alkyl, cycloalkyl, and aryl is attached to each phosphorus atom.

The bidentate phosphine ligand in the "transition metal complex catalyst containing at least one bidentate phosphine ligand" used in step A preferably contains two aromatic rings that are linked through an oxygen-containing linking group.

Examples of the "oxygen-containing linking group" include divalent groups, such as —O— and —$(CH_2)_{n1}$—O—$(CH_2)_{n2}$— wherein n1 and n2 are the same or different and each represent an integer of 0 to 6.

Examples of the aromatic ring include benzene ring.

The two aromatic rings may be further linked through another linking group in addition to the "oxygen-containing linking group."

The two aromatic rings each preferably have one phosphorus atom attached to one of the atoms constituting the ring.

Specific examples of "bidentate ligand" in the "transition metal complex catalyst containing at least one bidentate phosphine ligand" usable in step A include 1,2-bis(diphenylphosphino)ethane, 1,3-bis(diphenylphosphino)propane, 1,4-bis(diphenylphosphino)butane, 1,5-bis(diphenylphosphino)pentane, bis(diphenylphosphinophenyl)ether, bis(dicyclohexylphosphinophenyl)ether, 4,5-bis(diphenylphosphino)-9,9'-dimethylxanthene, 1,1'-bis(diphenylphosphino)ferrocene, 1,1'-bis(di-tert-butylphosphino)ferrocene, 1,1'-bis(dicyclohexylphosphino)ferrocene, 1,1'-bis(diisopropylphosphino)ferrocene, 2,2'-bis(diphenylphosphino)-1,1'-binaphthyl, 4,6-bis(diphenylphosphino)phenoxazine, 1,3-bis(diisopropylphosphino)propane, 1,4-bis(diisopropylphosphino)butane, 1,3-bis(dicyclohexylphosphino)propane, and 1,4-bis(dicyclohexylphosphino)butane.

The "transition metal complex catalyst containing at least one bidentate phosphine ligand" used in step A may contain at least one ligand other than the "bidentate phosphine ligand," and examples of such ligands include chlorine ligands.

Specific examples of the "transition metal complex catalyst containing at least one bidentate phosphine ligand" usable in step A include dichloro[1,2-bis(diphenylphosphino)ethane]palladium(II), dichloro[1,3-bis(diphenylphosphino)propane]palladium(II), dichloro[1,4-bis(diphenylphosphino)butane]palladium(II), dichloro[1,5-bis(diphenylphosphino)pentane]palladium(II), dichloro[bis(diphenylphosphinophenyl)ether]palladium(II), dichloro[bis(dicyclohexylphosphinophenyl)ether]palladium(II), dichloro[4,5-bis(diphenylphosphino)-9,9'-dimethylxanthene]palladium(II), dichloro[1,1'-bis(diphenylphosphino)ferrocene]palladium(II), dichloro[1,1'-bis(di-tert-butylphosphino)ferrocene]palladium(II), dichloro[1,1'-bis(dicyclohexylphosphino)ferrocene]palladium(II), dichloro[1,1'-bis(diisopropylphosphino)ferrocene]palladium(II), dichloro[2,2'-bis(diphenylphosphino)-1,1'-binaphthyl]palladium(II), dichloro[4,6-bis(diphenylphosphino)phenoxazine]palladium(II), dichloro[1,3-bis(diisopropylphosphino)propane]palladium(II), dichloro[1,4-bis(diisopropylphosphino)butane]palladium(II), dichloro[1,3-bis(dicyclohexylphosphino)propane]palladium(II), and dichloro[1,4-bis(dicyclohexylphosphino)butane]palladium(II).

The number of bidentate phosphine ligands coordinated to the transition metal varies depending on the oxidation number of the transition metal or other factors, but is preferably, for example, one or two.

The transition metal complex catalyst may be a reagent added to the reaction system, or a catalyst that is generated in the reaction system.

Preferable examples of precursors of transition metal complex catalysts generated in the reaction system include palladium chloride, palladium bromide, palladium acetate, bis(acetylacetonato)palladium(II), $Pd_2(dba)_3$ (dba represents dibenzylideneacetone), $Pd(COD)_2$ (COD represents cycloocta-1,5-diene), and $Pd(PPh_3)_4$ (Ph represents phenyl).

The "transition metal complex catalyst containing at least one bidentate phosphine ligand" used in step A may be a heterogeneous catalyst obtained by having the catalyst dispersed in or supported on a polymer, such as polystyrene and polyethylene.

Such a heterogeneous catalyst has advantages, for example, catalyst recovery, in the process. Examples of the specific structure of the catalyst include a structure in which a transition metal atom is immobilized by a polymer phosphine formed by introducing phosphines into a crosslinked polystyrene (PS) chain, as shown in the following chemical formula:

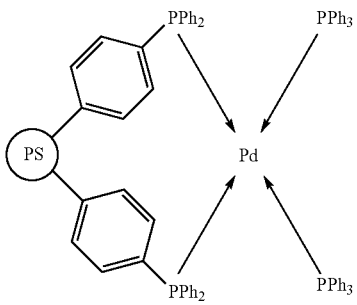

wherein PS represents polystyrene and Ph represents phenyl.

The "bidentate phosphine ligand" in this example is composed of triarylphosphines formed by binding one phenyl group of triphenylphosphine to a polymer chain as shown by the following chemical formula

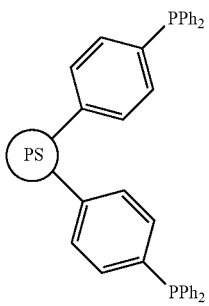

wherein PS represents polystyrene, and Ph represents phenyl.

The "transition metal complex catalyst containing at least one bidentate phosphine ligand" used in step A may be a supported catalyst in which the transition metal is supported on a carrier. Such a supported catalyst has a cost advantage because the catalyst is recyclable.

Examples of carriers include carbon, alumina, silica-alumina, silica, barium carbonate, barium sulfate, calcium carbonate, titanium oxide, zirconium oxide, and zeolite.

The upper limit of the amount of the transition metal catalyst is, for example, 0.05 moles, 0.01 moles, 0.005 moles, 0.002 moles, 0.001 moles, 0.0005 moles, 0.0001 moles, or 0.00006 moles per mole of the compound represented by formula (2).

The lower limit of the amount of the transition metal catalyst is typically 0.000001 moles, 0.00001 moles, and more preferably 0.00002 moles, or 0.00004 moles per mole of the compound represented by formula (2).

Step A is performed in the presence of a base.

Examples of bases usable in step A include amines, inorganic bases, and organic metal bases.

Examples of amines include triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, 1,8-diazabicyclo[5,4,0]-7-undecene, 1,5-diazabicyclo[4,3,0]-5-nonene, and 1,4-diazabicyclo[2,2,2]octane.

Examples of inorganic bases include lithium hydroxide, potassium hydroxide, sodium hydroxide, calcium hydroxide, lithium carbonate, sodium carbonate, potassium carbonate, sodium hydrogen carbonate, and potassium hydrogen carbonate.

Examples of organic metal bases include organic alkali metal compounds, such as butyllithium, t-butyllithium, phenyllithium, sodium triphenylmethyl, and sodium ethyl; organic alkali earth metal compounds, such as methylmagnesium bromide, dimethylmagnesium, phenylmagnesium chloride, phenylcalcium bromide, and bis(dicyclopentadiene)calcium; and alkoxides, such as sodium methoxide, and t-butyl methoxide.

Preferable examples of bases include lithium hydroxide, triethylamine, potassium carbonate, and lithium carbonate. More preferable examples of bases include triethylamine, potassium carbonate, and lithium carbonate. Particularly preferable examples of bases include triethylamine.

The bases can be used singly, or in a combination of two or more.

The amount of the base is typically 0.2 to 5 moles, and preferably about 0.5 to 3 moles per mole of the compound represented by formula (2).

Step A is performed at a temperature within the range of typically 10 to 150° C., preferably 50 to 120° C., more preferably 60 to 110° C., and still more preferably 70 to 110° C.

Performing step A at an excessively low temperature is likely to lower the starting material conversion and the yield.

When step A is performed at an excessively high temperature, the reaction mixture obtained after the reaction in step A may contain a starting material (i.e., the compound represented by formula (1)), by-products, or decomposition products, which may be observed in analysis conducted by the analysis described below.

Analysis Method

After completion of the reaction, hexafluorobenzene is added as an internal standard substance, and the resulting mixture is stirred. The mixture is then allowed to stand for a short period of time to precipitate the salt. The supernatant is diluted with deuterated chloroform, and subjected to quantification based on $^{19}$F-NMR integral values.

In step A, in addition to the alcohol represented by formula (3), which can also serve as a solvent, other solvent(s) may be used. When other solvent(s) are used, the amount of the alcohol represented by formula (3) can be reduced.

Examples of such solvents include non-aromatic hydrocarbon solvents, such as pentane, hexane, heptane, octane, cyclohexane, decahydronaphthalene, n-decane, isododecane, and tridecane; aromatic hydrocarbon solvents, such as benzene, toluene, xylene, tetralin, veratrole, diethylbenzene, methylnaphthalene, nitrobenzene, o-nitrotoluene, mesitylene, indene, and diphenyl sulfide; ketones, such as acetone, methyl ethyl ketone, methyl isobutyl ketone, acetophenone, propiophenone, diisobutyl ketone, and isophorone; halogenated hydrocarbon solvents, such as dichloromethane, chloroform, and chlorobenzene; ether solvents, such as diethyl ether, tetrahydrofuran, diisopropyl ether, methyl t-butyl ether, dioxane, dimethoxyethane, diglyme, phenetole, 1,1-dimethoxy cyclohexane, and diisoamyl ether; ester solvents, such as ethyl acetate, isopropyl acetate, diethyl malonate, 3-methoxy-3-methylbutyl acetate, γ-butyrolactone, ethylene carbonate, propylene carbonate, dimethyl carbonate, and α-acetyl-γ-butyrolactone; nitrile solvents, such as acetonitrile, and benzonitrile; sulfoxide-based solvents, such as dimethyl sulfoxide, and sulfolane; and amide solvents, such as N,N-dimethyl formamide, N,N-dimethyl acetamide, N-methylpyrrolidone, 1,3-dimethyl-2-imidazolidinone, N,N-dimethyl acrylic amide, N,N-dimethyl acetoacetoamide, N,N-diethyl formamide, and N,N-diethyl acetamide.

Preferable examples of solvents include ether solvents, such as diethyl ether, tetrahydrofuran, diisopropyl ether, methyl t-butyl ether, dioxane, dimethoxyethane, diglyme, phenetole, 1,1-dimethoxy cyclohexane, and diisoamyl ether; and amide solvents, such as N,N-dimethyl formamide, N,N-dimethyl acetamide, N-methylpyrrolidone, 1,3-dimethyl-2-imidazolidinone, N,N-dimethyl acrylic amide, N,N-dimethyl acetoacetoamide, N,N-diethyl formamide, and N,N-diethyl acetamide.

The solvent is preferably inert to the starting material compound, the catalyst, and the product in step A.

The solvents can be used singly, or in a combination of two or more.

When the compound represented by formula (1) has a low boiling point, the solvent for use is preferably an organic solvent having a high boiling point (e.g., 100° C. or more, more preferably 120° C. or more) from the standpoint of ease of compound purification. The use of such an organic solvent enables purification of the compound represented by formula (1) simply by distillation.

When the compound represented by formula (1) has a high boiling point, the use of a solvent having a low boiling point suitably enables purification of the compound represented by formula (1).

The amount of the solvent for use is not particularly limited as long as part or all of the starting materials are dissolved at the reaction temperature. For example, the solvent is used in an amount of 0.2 to 50 parts by weight, or 0.5 to 30 parts by weight per part by weight of the compound represented by formula (2).

Step A is preferably performed in the absence of water. The compound or reagent (e.g., a base such as an amine), and the solvent (which includes the alcohol represented by formula (3), which can serve as a solvent) all possibly containing water and used in step A are preferably dried before use. The drying treatment can be performed, for example, by using a distillation technique, a dehydrating agent such as a molecular sieve, a commercially available dehydrated solvent, or a combination thereof.

The use of a compound or reagent and/or a solvent that is not dried may reduce the yield and selectivity of the desired product, α-fluoroacrylic acid esters, because of the generation of α-fluoroacrylic acids as by-products.

Step A can be performed in the presence of a polymerization inhibitor. The polymerization inhibitor may be added before the reaction in step A or at a given point in time during the reaction in step A.

Examples of polymerization inhibitors include amine compounds, such as aliphatic primary amines, aliphatic secondary amines, aliphatic tertiary amines, alicyclic secondary amines, alicyclic tertiary amines, aromatic amines, heterocyclic amines, and polymer-supported amine compounds (polymeric amine compounds); ammonia; terpene compounds; and compounds containing at least one atom selected from the group consisting of oxygen and sulfur.

Examples of aliphatic primary amines include methylamine, ethylamine, propylamine, butylamine, pentylamine, hexylamine, cyclohexylamine, and ethylenediamine.

Examples of aliphatic secondary amines include dimethylamine, diethylamine, dipropylamine, dibutylamine, dipentylamine, dihexylamine, and dicyclohexylamine.

Examples of aliphatic tertiary amines include trimethylamine, triethylamine, diisopropylethylamine, tri(n-butyl)amine, and N,N,N',N'-tetramethylethylenediamine.

Examples of alicyclic secondary amines include piperidine, piperazine, pyrrolidine, and morpholine.

Examples of alicyclic tertiary amines include N-methylpiperazine, N-methylpyrrolidine, 1,5-diazabicyclo[4,3,0]-5-nonene, and 1,4-diazabicyclo[2,2,2]octane.

Examples of aromatic amines include aniline, methyl aniline, dimethylaniline, N,N-dimethylaniline, haloaniline, and nitroaniline.

Examples of heterocyclic amines include pyridine, melamine, pyrimidine, piperazine, quinoline, and imidazole.

Examples of polymer-supported amine compounds (polymeric amine compounds) include polyethyleneimine, polyallylamine, and polyvinylpyridine.

Examples of terpene compounds include α-pinene, camphene, α-terpinene, D-limonene, γ-terpinene, p-cymene, and terpinolene.

Preferable examples of compounds containing at least one atom selected from the group consisting of oxygen and sulfur include $C_{6-20}$ compounds containing at least one 6-membered aromatic carbocyclic ring and at least one oxygen atom or sulfur atom directly attached to at least one carbon atom constituting the ring structure(s) of the at least one 6-membered aromatic carbocyclic ring. Specific examples include hydroquinone, 4-methoxyphenol, 2,5-di-tert-butylhydroquinone, methylhydroquinone, tert-butylhydroquinone (TBH), p-benzoquinone, methyl-p-benzoquinone, tert-butyl-p-benzoquinone, 2,5-diphenyl-p-benzoquinone, 2,6-di-tert-butyl-4-methylphenol (BHT), and phenothiazine.

The amount of the polymerization inhibitor to be added is typically within the range of 0.0001 to 0.1 g, preferably 0.001 to 0.05 g, and more preferably 0.005 to 0.02 g per gram of the compound represented by formula (1). The polymerization inhibitor, when used in an amount within these ranges, can suitably function.

The time period for the reaction can be determined, for example, on the basis of the desired starting material conversion and yield. The specific time period is typically 1 to 24 hours, and preferably 6 to 18 hours.

The time period for the reaction can be shortened by applying a higher reaction temperature.

In the production process according to the present invention, the conversion of the starting material may be preferably 70% or more, more preferably 80% or more, and still more preferably 90% or more.

In the production process according to the present invention, the selectivity of the compound represented by formula (1) may be preferably 90% or more, and more preferably 95% or more.

In the production process according to the present invention, the yield of the compound represented by formula (1) may be preferably 85% or more, and more preferably 90% or more.

The compound represented by formula (1) obtained by the production process according to the present invention can optionally be purified by a known purification technique, such as solvent extraction, desiccation, filtration, distillation, condensation, and a mixture thereof.

In particular, since the production process according to the present invention generates only an extremely small amount of by-products and decomposed products, the process can provide a high-purity compound represented by formula (1) by using a simple technique such as distillation.

EXAMPLES

The following examples describe the present invention in more detail. However, the present invention is not limited to these examples.

Comparative Example 1

9.45 g (75.64 mmol) of 1-bromo-1-fluoroethene, 8.01 g (79.2 mmol) of triethylamine, 50.5 mg (0.072 mmol) of dichlorobis(triphenylphosphine)palladium(II), and 36 mL of methanol dried beforehand were placed in a 150-mL stainless autoclave, and 1.0 MPaG carbon monoxide was introduced thereto, followed by stirring at 100° C. for 14 hours.

After completion of the reaction, the autoclave was cooled, and the unreacted gas was purged. The autoclave was opened, and 186 mg (1.0 mmol) of hexafluorobenzene was added thereto as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 53.02 mmol (yield: 70.1%) of 2-fluoroacrylic acid methyl ester and 20.88 mmol (recovery: 27.6%) of unreacted 1-bromo-1-fluoroethene. The conversion was 72.5%, and the selectivity was 96.7%.

Example 1

8.76 g (70.11 mmol) of 1-bromo-1-fluoroethene, 8.01 g (79.2 mmol) of triethylamine, 51.5 mg (0.072 mmol) of dichloro[bis(diphenylphosphinophenyl)ether]palladium(II), and 36 mL of methanol dried beforehand were placed in a 150-mL stainless autoclave, and 1.0 MPaG carbon monoxide was introduced thereto, followed by stirring at 100° C. for 13 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 60.08 mmol (yield: 85.7%) of 2-fluoroacrylic acid methyl ester and 9.11 mmol (recovery: 13.0%) of unreacted 1-bromo-1-fluoroethene. The conversion was 86.8%, and the selectivity was 98.7%.

Example 2

8.88 g (71.07 mmol) of 1-bromo-1-fluoroethene, 8.01 g (79.2 mmol) of triethylamine, 54.4 mg (0.072 mmol) of dichloro[4,5-bis(diphenylphosphino)-9,9'-dimethylxanthene]palladium(II), and 36 mL of methanol dried beforehand were placed in a 150-mL stainless autoclave, and 1.0 MPaG carbon monoxide was introduced thereto, followed by stirring at 100° C. for 8 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 64.03 mmol (yield: 90.1%) of 2-fluoroacrylic acid methyl ester and 5.83 mmol (recovery: 8.2%) of unreacted 1-bromo-1-fluoroethene. The conversion was 91.0%, and the selectivity was 99.0%.

Example 3

9.11 g (72.93 mmol) of 1-bromo-1-fluoroethene, 8.01 g (79.2 mmol) of triethylamine, 54.4 mg (0.072 mmol) of dichloro[1,1'-bis(dicyclohexylphosphino)ferrocene]palladium(II), and 36 mL of methanol dried beforehand were placed in a 150-mL stainless autoclave, and 1.0 MPaG carbon monoxide was introduced thereto, followed by stirring at 100° C. for 12 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 65.27 mmol (yield: 89.5%) of 2-fluoroacrylic acid methyl ester and 7.07 mmol (recovery: 9.7%) of unreacted 1-bromo-1-fluoroethene. The conversion was 90.1%, and the selectivity was 99.3%.

Example 4

8.80 g (70.43 mmol) of 1-bromo-1-fluoroethene, 8.01 g (79.2 mmol) of triethylamine, 12.8 mg (0.072 mmol) of palladium chloride(II), 4.5 mg (0.072 mmol) of 2,2'-bis(diphenylphosphino)-1,1'-binaphthyl, and 36 mL of methanol dried beforehand were placed in a 150-mL stainless autoclave, and 1.0 MPaG carbon monoxide was introduced thereto, followed by stirring at 100° C. for 14 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 54.65 mmol (yield: 77.6%) of 2-fluoroacrylic acid methyl ester and 14.23 mmol (recovery: 20.2%) of unreacted 1-bromo-1-fluoroethene. The conversion was 78.9%, and the selectivity was 98.3%.

Example 5

9.14 g (73.16 mmol) of 1-bromo-1-fluoroethene, 8.01 g (79.2 mmol) of triethylamine, 12.8 mg (0.072 mmol) of palladium chloride(II), 32.4 mg (0.072 mmol) of 1,4-bis(dicyclohexylphosphino)butane, and 36 mL of methanol dried beforehand were placed in a 150-mL stainless autoclave, and 1.0 MPaG carbon monoxide was introduced thereto, followed by stirring at 100° C. for 14 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 58.09 mmol (yield: 79.4%) of 2-fluoroacrylic acid methyl ester and 13.46 mmol (recovery: 18.4%) of unreacted 1-bromo-1-fluoroethene. The conversion was 81.0%, and the selectivity was 98.0%.

Example 6

8.95 g (71.63 mmol) of 1-bromo-1-fluoroethene, 8.01 g (79.2 mmol) of triethylamine, 2.7 mg (0.0036 mmol) of dichloro[4,5-bis(diphenylphosphino)-9,9'-dimethylxanthene]palladium(II), and 36 mL of methanol dried beforehand were placed in a 150-mL stainless autoclave, and 1.0 MPaG carbon monoxide was introduced thereto, followed by stirring at 100° C. for 8 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 59.81 mmol (yield: 83.5%) of 2-fluoroacrylic acid methyl ester and 10.60 mmol (recovery: 14.8%) of unreacted 1-bromo-1-fluoroethene. The conversion was 84.9%, and the selectivity was 98.3%.

Example 7

9.02 g (72.19 mmol) of 1-bromo-1-fluoroethene, 8.01 g (79.2 mmol) of triethylamine, 54.4 mg (0.072 mmol) of dichloro[4,5-bis(diphenylphosphino)-9,9'-dimethylxanthene]palladium(II), and 36 mL of ethanol dried beforehand were placed in a 150-mL stainless autoclave, and 1.0 MPaG carbon monoxide was introduced thereto, followed by stirring at 100° C. for 8 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 63.46 mmol (yield: 87.9%) of 2-fluoroacrylic acid ethyl ester and 7.29 mmol (recovery: 10.1%) of unreacted 1-bromo-1-fluoroethene. The conversion was 88.6%, and the selectivity was 99.2%.

Example 8

8.86 g (70.91 mmol) of 1-bromo-1-fluoroethene, 8.01 g (79.2 mmol) of triethylamine, 54.4 mg (0.072 mmol) of dichloro[4,5-bis(diphenylphosphino)-9,9'-dimethylxanthene]palladium(II), 4.61 g (0.144 moL) of methanol, and 36 mL of tetrahydrofuran dried beforehand were placed in a 150-mL stainless autoclave, and 1.0 MPaG carbon monoxide was introduced thereto, followed by stirring at 100° C. for 7 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 60.42 mmol (yield 85.2%) of 2-fluoroacrylic acid methyl ester and 9.43 mmol (recovery: 13.3%) of unreacted 1-bromo-1-fluoroethene. The conversion was 86.0%, and the selectivity was 99.1%.

Example 9

8.94 g (71.55 mmol) of 1-bromo-1-fluoroethene, 8.01 g (79.2 mmol) of triethylamine, 54.4 mg (0.072 mmol) of dichloro[4,5-bis(diphenylphosphino)-9,9'-dimethylxanthene]palladium(II), 4.61 g (0.144 moL) of methanol, and 36 mL of N-methylpyrrolidone dried beforehand were placed in a 150-mL stainless autoclave, and 1.0 MPaG carbon monoxide was introduced thereto, followed by stirring at 100° C. for 7 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 62.75 mmol (yield: 87.7%) of 2-fluoroacrylic acid methyl ester and 7.01 mmol (recovery: 9.8%) of unreacted 1-bromo-1-fluoroethene. The conversion was 89.1%, and the selectivity was 98.4%.

Example 10

7.12 g (35.4 mmol) of 2-bromo-2-fluorovinylbenzene, 4.01 g (39.6 mmol) of triethylamine, 27.2 mg (0.036 mmol) of dichloro[4,5-bis(diphenylphosphino)-9,9'-dimethylxanthene]palladium(II), and 18 mL of methanol dried beforehand were placed in a 150-mL stainless autoclave, and 1.0 MPaG carbon monoxide was introduced thereto, followed by stirring at 100° C. for 9 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 32.64 mmol (yield: 92.2%) of 2-fluoro-3-phenyl acrylic acid methyl ester and 1.88 mmol (recovery: 5.3%) of unreacted 2-bromo-2-fluorovinylbenzene. The conversion was 93.6%, and the selectivity was 98.5%.

Example 11

8.11 g (35.1 mmol) of 1-(2-bromo-2-fluorovinyl)-4-methoxybenzene, 4.01 g (39.6 mmol) of triethylamine, 27.2 mg (0.036 mmol) of dichloro[4,5-bis(diphenylphosphino)-9,9'-dimethylxanthene]palladium(II), and 18 mL of ethanol dried beforehand were placed in a 150-mL stainless autoclave, and 1.0 MPaG carbon monoxide was introduced thereto, followed by stirring at 100° C. for 9 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 30.54 mmol (yield: 87.0%) of 2-fluoro-3-(4-methoxyphenyl)acrylic acid ethyl ester and 3.47 mmol (recovery: 9.9%) of unreacted 1-(2-bromo-2-fluorovinyl)-4-methoxybenzene. The conversion was 89.3%, and the selectivity was 97.4%.

Example 12

8.98 g (71.87 mmol) of 1-bromo-1-fluoroethene, 8.01 g (79.2 mmol) of triethylamine, 51.5 mg (0.072 mmol) of dichloro[bis(diphenylphosphinophenyl)ether]palladium(II), and 36 mL of non-dried methanol were placed in a 150-mL stainless autoclave, and 1.0 MPaG carbon monoxide was introduced thereto, followed by stirring at 100° C. for 13 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 50.93 mmol (yield: 70.9%) of 2-fluoroacrylic acid methyl ester, 10.13 mmol (yield: 14.1%) of 2-fluoroacrylic acid, and 8.12 mmol (recovery: 11.3%) of unreacted 1-bromo-1-fluoroethene. The conversion was 87.5%, and the selectivity was 81.0%.

Example 13

8.89 g (71.15 mmol) of 1-bromo-1-fluoroethene, 8.01 g (79.2 mmol) of triethylamine, 51.5 mg (0.072 mmol) of dichloro[bis(diphenylphosphinophenyl)ether]palladium(II), 75.0 mg (0.34 mmol) of 2,6-di-tert-butyl-4-methylphenol, and 36 mL of methanol dried beforehand were placed in a 150-mL stainless autoclave, and 1.0 MPaG carbon monoxide was introduced thereto, followed by stirring at 100° C. for 13 hours.

After completion of the reaction, the autoclave was cooled, and the unreacted gas was purged. The autoclave was opened, and 186 mg (1.0 mmol) of hexafluorobenzene was added as an internal standard substance, followed by stirring. The mixture was then allowed to stand for a short period of time to precipitate the salt. The supernatant was diluted with deuterated chloroform, and subjected to quantification based on $^{19}$F-NMR integral values. The diluted supernatant was found to contain 62.85 mmol (yield: 88.3%) of 2-fluoroacrylic acid methyl ester and 6.81 mmol (recovery: 9.6%) of unreacted 1-bromo-1-fluoroethene. The conversion was 90.4%, and the selectivity was 97.7%.

INDUSTRIAL APPLICABILITY

The present invention enables the production of α-fluoroacrylic acid esters useful as intermediates for synthesis at a high starting material conversion and a high yield.

The invention claimed is:

1. A process for producing a compound of formula (1):

wherein $R^1$ and $R^2$ are the same or different and each is alkyl, fluoroalkyl, aryl optionally substituted with at least one substituent, halogen, or hydrogen; and $R^3$ is alkyl, fluoroalkyl, or aryl optionally substituted with at least one substituent, the process comprising step A of reacting a compound of formula (2):

wherein the symbols are as defined above, with carbon monoxide and an alcohol of formula (3):

wherein the symbol is as defined above, in the presence of a palladium complex catalyst containing at least one bidentate phosphine ligand and a base to thereby obtain the compound of formula (1).

2. The process according to claim 1, wherein $R^1$ is hydrogen or aryl, and $R^2$ is hydrogen or aryl.

3. The process according to claim 1, wherein the at least one bidentate phosphine ligand contains two aromatic rings that are linked through an oxygen-containing linking group.

4. The process according to claim 1, wherein the palladium complex catalyst is used in an amount of 0.001 moles or less per mole of the compound of formula (2).

5. The process according to claim 1, wherein the base is an amine.

6. The process according to claim 1, wherein step A is performed at a temperature within the range of 60 to 120° C.

* * * * *